United States Patent
Forester et al.

(10) Patent No.: US 6,362,374 B1
(45) Date of Patent: Mar. 26, 2002

(54) COMPOSITION OF AND METHOD FOR POLYSULFIDES HAVING A REDUCED ODOR LEVEL

(75) Inventors: David R. Forester, Concord Township; Roger L. Sowerby, Concord; Bharat B. Malik; Victor A. Gober, both of Euclid, all of OH (US)

(73) Assignee: The Lubrizol Corporation, Wickliffe, OH (US)

( * ) Notice: Subject to any disclaimer, the term of this patent is extended or adjusted under 35 U.S.C. 154(b) by 0 days.

(21) Appl. No.: 09/563,040

(22) Filed: May 1, 2000

(51) Int. Cl.[7] .............................................. C07C 321/00
(52) U.S. Cl. ....................................................... 568/21
(58) Field of Search .................................... 568/21, 25

(56) References Cited

U.S. PATENT DOCUMENTS

| | | | |
|---|---|---|---|
| 4,119,549 A | 10/1978 | Davis | 252/45 |
| 4,340,707 A | 7/1982 | Qüis et al. | 526/289 |
| 5,008,432 A | 4/1991 | Roberts | 558/436 |
| 5,152,909 A | * 10/1992 | Tipton | |
| 5,559,271 A | * 9/1996 | Shaw et al. | 568/21 |

FOREIGN PATENT DOCUMENTS

| | | |
|---|---|---|
| EP | 976726 A1 | 2/2000 |
| JP | 8-245562 | 9/1996 |

OTHER PUBLICATIONS

CA:66:2835 abs of J Polym Chem Ed by Sugimura et al 4(11) pp 2747–2756, 1966.*
CA:93:170914 abs of FR2434864, Mar. 1980.*
CA:93:189037 abs of FR2434863, Mar. 1980.*
CA:94:121290 abs of JP55094378, Jul. 1980.*
Chemical Abstract Accession No. 1981–624875 (1981).
Chemical Abstract Accession No. 1983–773692 (1983).

* cited by examiner

Primary Examiner—Jean F. Vollano
(74) Attorney, Agent, or Firm—Jeffrey F. Munson; Sameul B. Laferty; Joseph P. Fischer

(57) ABSTRACT

The present invention is directed to a composition that contains polysulfides and that has a reduced odor level and to a method for reducing the odor of polysulfides. The composition contains a polysulfide and an inhibitor that reduces the odor level. The polysulfides include sulfurized olefins prepared by reacting the olefin with sulfur and $H_2S$ in the presence of a catalyst. The inhibitors are selected from the group consisting of hydrocarbyl acrylates and hydrocarbyl methacrylates. The method for reducing the odor level of polysulfides involves contacting the polysulfide with an inhibitor selected from the group consisting of hydrocarbyl acrylates and hydrocarbyl methacrylates under conditions that reduce the odor level.

8 Claims, No Drawings

COMPOSITION OF AND METHOD FOR POLYSULFIDES HAVING A REDUCED ODOR LEVEL

BACKGROUND OF THE INVENTION

1. Field of the Invention

The present invention involves a composition containing polysulfides and inhibitors that has a reduced odor level, and a method to reduce the odor level of polysulfides. These polysulfide compositions with a reduced odor level are more useful in various commercial applications such as metalworking fluids.

2. Description of the Related Art

Polysulfides have been found to provide many useful functions in various areas of commerce.

Polysulfides can function as antiwear agents, extreme-pressure agents and antioxidants in lubricants such as gear oils and metalworking fluids. Polysulfides can also function as presulfiding agents for hydrotreating and hydrocracking catalysts used in refinery operations. Polysulfides can also find use as vulcanization agents in the production of elastomers and as metal passivation agents for use in high-temperature furnace operations.

Most of these areas of use require polysulfides that have a high sulfur content and corresponding increase in the higher and less stable polysulfide homologues, starting with tetrasulfides on up, in addition to increased levels of $H_2S$ (hydrogen sulfide) and unreacted or free sulfur. These high sulfur content polysulfides can generate $H_2S$ upon storage. The presence of this $H_2S$ contributes to an obnoxious odor and, above threshold limits, becomes a safety and environmental hazard because $H_2S$ is toxic and flammable. In addition, $H_2S$ is an irritant. Consequently, polysulfides having a reduced odor level and methods to reduce the odor level of polysulfides are highly desirable.

Japanese Patent Application 8,245,562, published on Sep. 24, 1996, discloses the use of methyl acrylate as a $H_2S$ scavenger for the production of an alkyl isothiocyanate from an alkyl dithiocarbamate precursor by treating the carbamate precursor with the acrylate.

U.S. Pat. No. 5,008,432, issued on Apr. 16, 1991, deals with the production of mercaptan-containing compounds by reacting a compound having an activated, olefinic double bond such as methyl acrylate with $H_2S$ in the presence of a catalyst.

U.S. Pat. No. 4,340,707, issued Jul. 20, 1982, involves oligomers as intermediates to UV-hardenable binders or coatings that are prepared by reacting $H_2S$ or polyfunctional mercaptans with polyfunctional acrylates.

Using the method of the present invention to reduce the odor level of polysulfides to acceptable levels, based on odor and safety and environmental criteria, gives polysulfide compositions that are readily useful in various applications. The polysulfide compositions of the present invention generally include a non-nitrogen-containing inhibitor that can be advantageous for use as presulfiding agents of refinery catalysts and as metal passivation agents in high-temperature furnace operations.

SUMMARY OF THE INVENTION

The present invention provides a method for reducing the odor level of a polysulfide composition.

The present invention is also directed to a composition having a reduced odor level comprising a polysulfide and an inhibitor selected from the group consisting of hydrocarbyl acrylates and hydrocarbyl methacrylates.

In another embodiment of the present invention, the polysulfide of the composition having a reduced odor level is the reaction product of an olefin selected from the group consisting of isobutylene and diisobutylene with sulfur and $H_2S$ in the presence of a catalyst.

In a further embodiment of the present invention, a method for reducing the odor level of a polysulfide comprises contacting the polysulfide with an inhibitor selected from the group consisting of hydrocarbyl acrylates and hydrocarbyl methacrylates under conditions that reduce the odor.

In a still further embodiment of the present invention, the polysulfide in the method for reducing the odor level is the reaction product of an olefin selected from the group consisting of isobutylene and diisobutylene with sulfur and $H_2S$ in the presence of a catalyst.

Additional objects and advantages of the present invention will be set forth in part in the description that follows and in part will be obvious from the description or may be learned by practice of this invention. The objects and advantages of the invention may be realized and attained by means of the instrumentalities pointed out in the appended claims.

DETAILED DESCRIPTION OF THE INVENTION

The composition of the present invention comprises as a first component a polysulfide. The polysulfides of the present invention are sulfur-containing organic compositions that contain one or more sulfur linkages that can be represented by the formula —S— where S is sulfur and x is a number greater than one. These sulfur-containing organic compositions can be acyclic or cyclic. The organic portion of these compositions has a hydrocarbyl makeup; that is, it is predominately hydrocarbon in nature but may have non-hydrocarbon substituent groups and may contain heteroatoms in addition to sulfur.

The polysulfides of the present invention are generally obtained by sulfurizing starting materials using a sulfur source. The starting materials are organic compositions containing one or more olefinic double bonds; that is, double bonds connecting two aliphatic carbon atoms. Examples of organic compositions containing one or more olefinic double bonds are acyclic and cyclic olefins, acyclic polyenes such as 1,4-butadiene and isoprene, cyclic polyenes, unsaturated carboxylic acids and esters, unsaturated fats and oils from plants and animals, and mixtures thereof. Preferred starting materials for the polysulfides of the present invention are isobutylene, diisobutylene and $C_8$ and higher alpha-olefins and their corresponding structural and geometric isomers including the octenes, the nonenes, the hexadecenes, the octadecenes, the tetracosenes, and the heptacosenes. The sulfur source can be sulfur, sulfur halides such as $SCl_2$ or $S_2Cl_2$, $H_2S$, polysulfide salts, and mixtures thereof. A preferred sulfur source for polysulfides of the present invention is a mixture of sulfur and $H_2S$.

The polysulfides of the present invention can be prepared by contacting the starting materials with the sulfur source under conditions that result in the formation of polysulfides. A preferred preparation method for the polysulfides of the present invention involves reacting isobutylene or diisobutylene with sulfur and $H_2S$ in the presence a catalyst. A preferred catalyst is n-butylamine. Preparation methods for polysulfides of the present invention are presented in U.S. Pat. Nos. 4,119,549 and 4,873,006, the disclosures of which are incorporated herein by reference.

The polysulfides of the present invention can also be prepared by reacting a mercaptan with sulfur in the presence of a basic catalyst as presented in U.S. Pat. No. 5,530,163, the disclosure of which is incorporated herein by reference.

The composition of the present invention comprises, as a second component, an inhibitor selected from the group consisting of hydrocarbyl acrylates and hydrocarbyl methacrylates. The hydrocarbyl group is predominately hydrocarbon in nature but may have nonhydrocarbon substituent groups and may contain heteroatoms such as oxygen. Preferred nonhydrocarbon substituent groups are cyclic ether groups such as epoxy groups represented by the formula

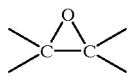

and hydroxy groups. The hydrocarbyl group is preferably a $C_2$ to $C_{20}$ hydrocarbyl group or mixtures thereof. The inhibitors can be monoacrylates, monomethacrylates, polyacrylates or polymethacrylates. Examples of inhibitors of the present invention are 2-ethylhexyl acrylate, 2,6-dimethylheptyl methacrylate, isodecyl methacrylate, n-dodecyl acrylate, C12-18 acrylate, ethylene glycol dimethacrylate, 1,6-hexanediol diacrylate, trimethylolpropane triacrylate, propoxylated neopentyl glycol diacrylate (available from Sartomer as SR-9003 OLIGOMER®), tetraethylene glycol diacrylate, poly(ethylene glycol) 200 monomethyl ether monomethacrylate, poly(ethylene glycol) 400 monomethyl ether monomethacrylate, glycidyl methacrylate, 2-hydroxyethyl acrylate, and 2-hydroxyethyl methacrylate.

The method of the present invention for reducing the odor level of a polysulfide comprises contacting the polysulfide with an inhibitor selected from the group consisting of hydrocarbyl acrylates and hydrocarbyl methacrylates under conditions that reduce the odor level.

In a preferred method the hydrocarbyl group of the inhibitor is a $C_2$ to $C_{20}$ hydrocarbyl group or mixtures thereof such as n-dodecyl acrylate or glycidyl methacrylate.

In a preferred method the polysulfide is the reaction product of an olefin selected from isobutylene and diisobutylene with sulfur and $H_2S$ using a catalyst.

The conditions in the method of the present invention for reducing the odor level of a polysulfide involve contacting or mixing the polysulfide with an inhibitor where preferred conditions are a polysulfide-to-inhibitor weight ratio of 90:10 to 99.9:0.1, a period of 5 minutes to 2 hours, and a temperature of 10 to 80° C. More preferred conditions are a polysulfide-to-inhibitor weight ratio of 95:5 to 99.9:0.1, a period of 0.25 to 1.5 hours, and a temperature of 15 to 75° C. Most preferred conditions are a polysulfide-to-inhibitor weight ratio of 98:2 to 99.9:0.1, a period of 0.5 to 1 hour, and a temperature of 20 to 70° C.

The method and composition of the present invention provide polysulfides having a reduced odor level. These polysulfides can be readily used in various applications including aqueous and nonaqueous metalworking fluids, automotive and industrial gear oils, as presulfiding agents for catalysts used in refinery operations, and as metal passivation agents for use in high-temperature furnace operations.

The following examples are illustrative of the methods and compositions of the present invention but are not limiting on the scope of the invention as defined by the appended claims.

EXAMPLE 1

A polysulfide containing 36.6% S by weight was prepared by reacting diisobutylene with sulfur and $H_2S$ using n-butylamine as a catalyst. A portion of this polysulfide was treated by mixing with n-dodecyl acrylate (available from Aldrich, Ciba Geigy, or Sartomer) in a weight ratio of polysulfide to acrylate of 99.5:0.5 for 0.5 hour at 66° C. After storage for 10 days at 60° C., the untreated polysulfide gave 14.5 ppm $H_2S$ while the treated polysulfide gave 6.9 ppm $H_2S$ as measured by a GC headspace analyzer using a sulfur-specific detector. A portion of the polysulfide treated in the same way with a nitrogen-containing inhibitor (available from Baker Petrolite as TOLAD 9220®) gave 1.6 ppm $H_2S$ per GC analysis after storage for 10 days at 60° C.

EXAMPLE 1A

A polysulfide containing 38% S by weight was prepared by reacting diisobutylene with sulfur and $H_2S$ using n-butylamine as a catalyst. A portion of this polysulfide was treated with n-dodecyl acrylate in the same way as in Example 1. After storage for 10 days at 60° C., the untreated polysulfide gave 51 ppm $H_2S$ while the treated polysulfide gave 4.7 ppm $H_2S$ per GC analysis.

EXAMPLE 2

A polysulfide containing 54% S by weight was prepared by reacting isobutylene with sulfur and $H_2S$ using n-butylamine as a catalyst. Portions of this polysulfide were treated with glycidyl methacrylate (available from San Esters) or a nitrogen-containing inhibitor (available from Baker Petrolite as TOLAD SX-9200®) by mixing in a weight ratio of polysulfide to inhibitor of 99.6:0.4 for about 1 hour at 20° C. After storage for 12 days at 60° C., the untreated polysulfide gave 38 ppm $H_2S$, the methacrylate-treated polysulfide gave 0.5 ppm $H_2S$, and the TOLAD SX-9200®-treated polysulfide gave <0.1 ppm $H_2S$ per GC analysis.

What is claimed is:
1. A composition having a reduced odor level, comprising:
   a polysulfide; and
   an inhibitor selected from the group consisting of hydrocarbyl acrylates and hydrocarbyl methacrylates wherein the polysulfide is a sulfur-containing organic composition, the hydrocarbyl group of the inhibitor is a $C_2$ to $C_{20}$ hydrocarbyl group or mixtures thereof, and the polysulfide-to-inhibitor weight ratio is 95:5 to 99.9:0.1.

2. The composition of claim 1, wherein the polysulfide is the reaction product of an olefin selected from the group consisting of isobutylene and diisobutylene with sulfur and $H_2S$ in the presence of a catalyst.

3. The composition of claim 2, wherein the inhibitor is n-dodecyl acrylate, or glycidyl methacrylate.

4. A method for reducing the odor level of a polysulfide, comprising:

contacting the polysulfide with an inhibitor selected from the group consisting of hydrocarbyl acrylates and hydrocarbyl methacrylates under conditions that reduce the odor level wherein the conditions are contacting or mixing the polysulfide with the inhibitor in a polysulfide-to-inhibitor weight ratio of 90:10 to 99.9:0.1 for a period of 5 minutes to 2 hours at a temperature of 10 to 80° C.

5. The method of claim 4, wherein the polysulfide is the reaction product of an olefin selected from the group consisting of isobutylene and diisobutylene with sulfur and $H_2S$ in the presence of a catalyst.

6. The method of claim 4, wherein the hydrocarbyl group of the inhibitor is a $C_2$–$C_{20}$ hydrocarbyl group or mixtures thereof.

7. The method of claim 4, wherein the polysulfide-to-inhibitor weight ratio is 95:5 to 99.9:0.1.

8. The method of claim 5, wherein the inhibitor is n-dodecyl acrylate, or glycidyl methacrylate.

* * * * *